United States Patent [19]
North, Jr.

[11] Patent Number: 4,461,181
[45] Date of Patent: Jul. 24, 1984

[54] CONTROL FOR SAMPLE VOLUME METERING APPARATUS

[75] Inventor: Howard L. North, Jr., Newfoundland, N.J.

[73] Assignee: Becton Dickinson and Company, Paramus, N.J.

[21] Appl. No.: 456,175

[22] Filed: Jan. 6, 1983

[51] Int. Cl.³ .................. G01L 7/18; H01H 29/28
[52] U.S. Cl. ............................... 73/749; 73/706; 200/81.6; 324/71.4
[58] Field of Search ............... 73/706, 747, 748, 749; 324/71.4; 377/11, 12; 200/81.6, 83 Q, 83 Y

[56] References Cited

U.S. PATENT DOCUMENTS

| | | |
|---|---|---|
| 1,642,615 | 9/1927 | Lommel . |
| 1,917,637 | 7/1933 | Dwyer ............................. 73/747 |
| 1,997,437 | 4/1935 | Smith . |
| 2,475,602 | 7/1949 | Forst . |
| 2,819,616 | 1/1958 | Hinkle . |
| 2,869,078 | 1/1959 | Coulter . |
| 3,122,924 | 3/1964 | Pall . |
| 3,208,284 | 9/1965 | Rivero ............................. 73/706 |
| 3,248,948 | 5/1966 | Keller . |
| 3,433,077 | 3/1969 | Gilmont . |
| 3,446,076 | 5/1969 | Dieterich ......................... 73/747 |
| 3,492,871 | 2/1970 | Rainero . |
| 3,541,858 | 11/1970 | Bonczek . |
| 3,611,811 | 10/1971 | Lissau . |
| 3,921,006 | 11/1975 | Pontigny . |

*Primary Examiner*—S. Clement Swisher
*Attorney, Agent, or Firm*—R. P. Grindle

[57] ABSTRACT

A manometer is provided for metering samples of fluid flowing in devices wherein particle concentration in the fluid is being counted or measured. Such devices include particle counters for determining blood cell concentration in body fluid. The device includes low permeable stretchable diaphragms in the device connections for containing the mercury therein, and a slide valve in the vent connection to restrict the movement of the mercury during storage or shipment. The arrangement herein includes, also, a one-way valve downstream of the "stop" point to stop flow substantially immediately upon the cessation of the measurement interval to reduce unwanted airflow to the counting aperture. A start and stop arrangement in the mercury flow path for causing the leading edge of the mercury meniscus at the axis thereof to engage the electrode contacts includes simple wire tips extending into the mercury flow path to the axis thereof for engaging the axis of the mercury meniscus. A preset fixed sample volume metering chamber is provided which eliminates the need for calibration.

9 Claims, 3 Drawing Figures

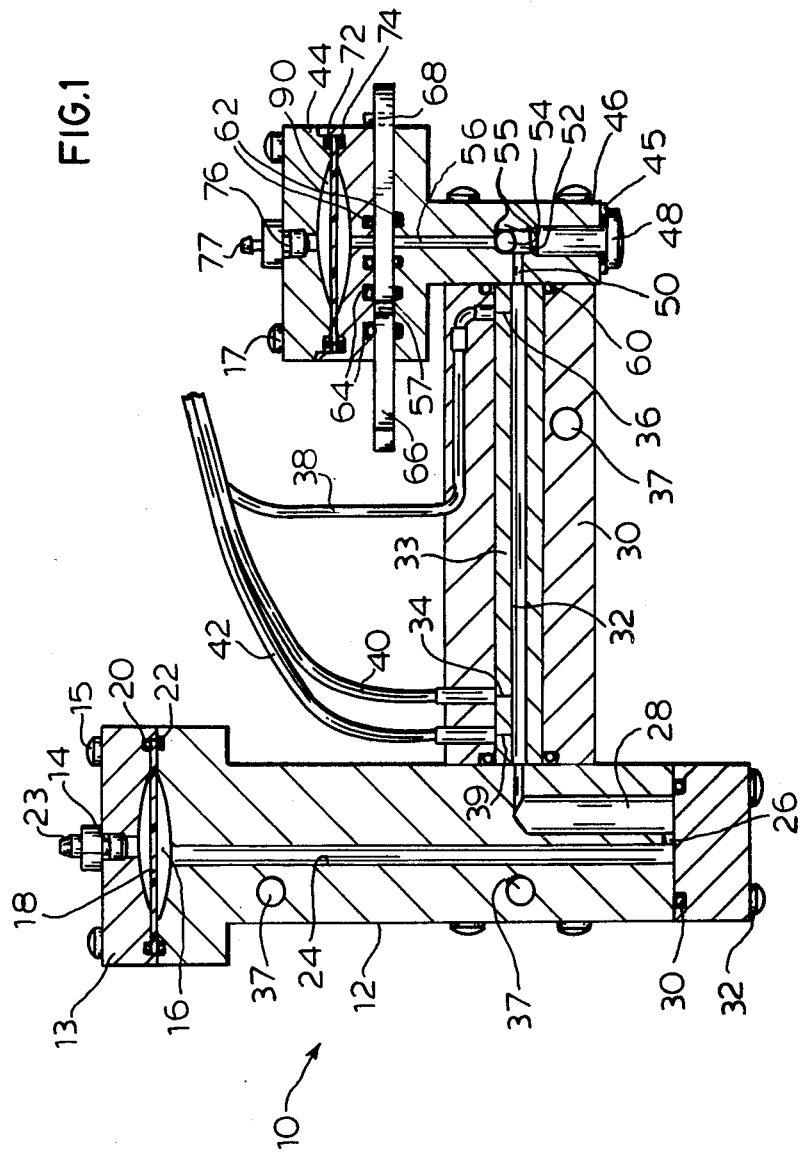

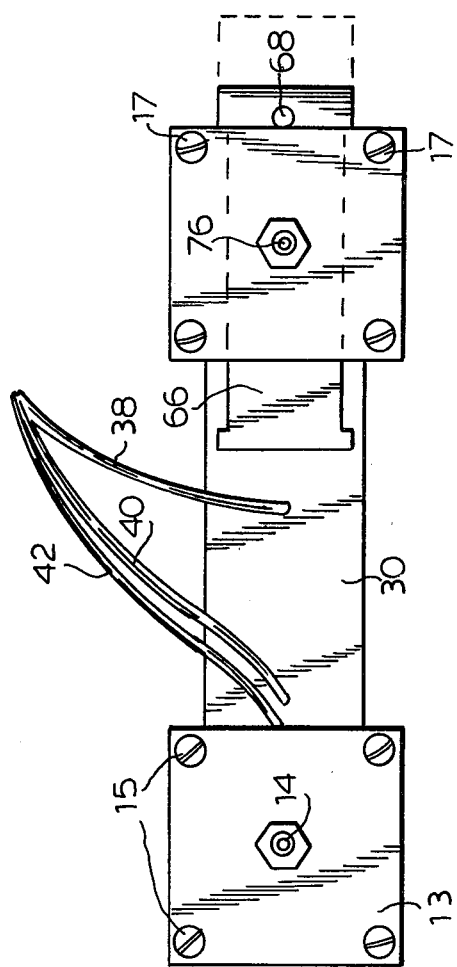

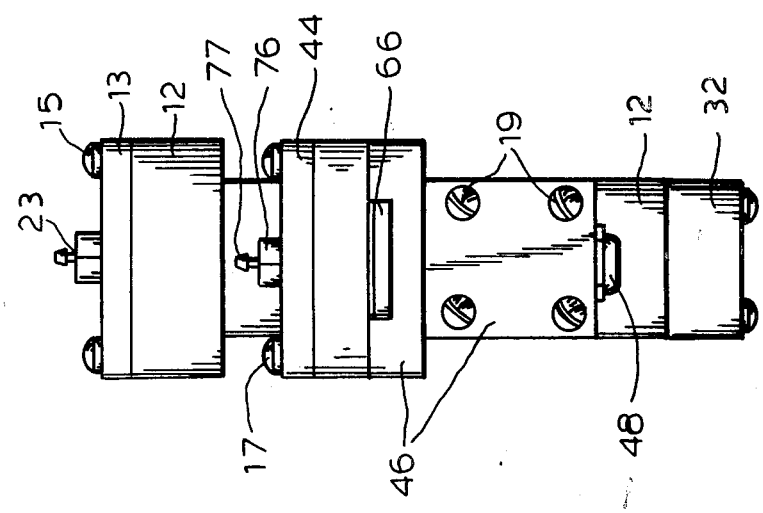

CONTROL FOR SAMPLE VOLUME METERING APPARATUS

BACKGROUND AND STATEMENT OF THE INVENTION

This invention relates generally to devices for metering liquids. More particularly, this invention relates to metering apparatus for metering repeated equal constant volumes of fluid samples.

In counting particles or other materials such as blood cells suspended in a fluid medium, it will be appreciated that it is necessary that a precise degree of control be carried out in the flow of the liquid suspension being examined. That is, the degree of control of the flow of the material affects the accuracy of the determination. In blood cell counters, it is necessary to accurately and precisely control and measure the flow of the sample suspension past the scanning point of the detecting system so that a constant volume of the sample suspension is metered through the detecting system. A high order of repeatability of flow of the sample suspension through the detecting system, especially of different suspensions, is particularly desirable in the interest of efficiency and economy. It will be appreciated, further, that changes in the metered volume of a sample suspension due to outside influences such as ordinary temperature changes must be accommodated.

Thus, it is the object of this invention to provide a novel fluid metering apparatus which enables a more precise and accurate metering of a pre-determined and constant volume of the fluid to be tested as it passes the scanning point of a detecting system than has been realized in the past.

The above is achieved, in accordance with this invention, by the use of low permeability elastomeric diaphragms in the vent and sample volume connections of the manometer of the invention in order to isolate the mercury contained therein from contamination, and to reduce the necessity of having to clean the instrument. Moreover, a one-way valve is utilized in the air vent stack of the manometer which valve closes off the flow of mercury almost immediately after the mercury meniscus passes the "stop" point in the measurement cycle. The purpose of the one-way valve is to reduce to a minimum air flow into the counting aperture, once the counting period has ceased. The valve causes immediate cessation of flow once the measuring function has taken place. The valve may be a ball valve comprised of a material inert to mercury such as, for example, polytetrafluoroethylene.

Also provided in accordance with this invention is the use of a slide valve for closing off the vent stack and isolating the mercury from the vent diaphragm cavity during shipping. This has the effect of restricting the movement of the mercury during any jolting going on during shipment or in the storage and handling of a manometer.

Additionally, the start and stop points in the mercury flow path of the manometer of the invention are simple wire tips extending into the mercury flow passage for engaging the axis of the mercury meniscus. This provides a much more precise initiation and cessation of the counting or metering period. In this connection, the electrode contacts may be, for example, molybdenum contact wires having an amalgam of mercury at the contact ends thereof in order to produce a mercury-to-mercury contact. Such a contact is self-renewing, thus making the instrument, in accordance herewith much more precise and long lasting.

A further important feature of the invention is a pre-set fixed volume sample or metering tube which is positioned horizontally so as to eliminate the need for calibration. That is, because of the preset volume of the tube, no calibration is necessary. In this connection, the substantially horizontal sample tube is positioned deliberately with a slight tilt between the start and stop count electrodes so that the very minor change in height of the medium when it passes through the conduit balances the change in pressure due to the diaphragm displacements at either end of the instrument.

This has the effect of satisfying a range of volume compliance values which is the result of a change in the vacuum applied to the aperture system during the counting period. This changing pressure multiplied by the system volume compliance, yields a volume change of the conduits and their contents, (including air) which means that the volume measured by the manometer is not identical to the volume of a sample drawn through the aperture of the counting instrument being metered. Thus, there is an error in volume measurement. The slight tilting to accommodate this volume compliance has the effect of overcoming this phenomenon.

Other objects and advantages of this invention will be apparent from the following description, the accompanying drawings, and the appended claims.

DESCRIPTION OF THE DRAWINGS

FIG. 1 is a longitudinal sectional view of a manometer illustrating the invention;

FIG. 2 is a top plan view of the manometer of FIG. 1; and

FIG. 3 is a side elevation view of the manometer of FIG. 1 as viewed from the right hand end thereof.

DETAILED DESCRIPTION OF THE INVENTION

Referring to the drawings in which like reference characters refer to like parts throughout the several views thereof, the manometer of the invention is designated generally 10 in FIG. 1. A medical diagnostic procedure includes analyzing and testing blood samples of a patient in order to make certain classic determinations relative to the blood sample. Instrumentation which will accept a patient's blood sample and process the sample automatically and continuously is described in U.S. Pat. Nos. 4,282,902; 4,165,484; 4,240,029 and 4,110,604. The manometer described and claimed in this application is suitable for use in such instrumentation as described in these patents, as well as other electronic particle counting instrumentation such as that described and claimed in U.S. Pat. No. 2,869,078, for example.

Referring further to FIG. 1, the manometer 10 includes a sample volume connection stack 12 to which a top 13 is bolted by bolts 15, as shown in FIG. 2. Stack 12 and top 13 incorporate therebetween a sample volume connection cavity 16 in which is placed a low permeable elastic diaphragm 18, the outer edges of which are held in place by upper and lower O rings 20, 22. Diaphragm 18 is impermeable to mercury contained in sample volume stack 12, so as to contain the mercury therein against any undue movement of the mercury in passage 24 in stack 12. Diaphragm 18 possesses a stretchable property in order to "give" if the mercury rises in stack 12, but still contains the mercury therein.

Diaphragm 18 is pervious to the passage of air in order to allow the passage of oxygen, nitrogen, carbon dioxide, carbon monoxide, water vapor, hydrocarbons and other gases therethrough. The material selected for the diaphragm will, however, be impervious to sulfur containing gases such as sulfur oxides and hydrogen sulfide which will pollute mercury contained in the manometer of the invention.

As can be seen in FIG. 1, sample volume stack 12 includes an inlet 14 around fitting 23 leading to cavity 16. The stack includes a vertical passage 24, as discussed above, which leads from cavity 16 to passage 26 at the bottom of stack 12. Passage 26, in turn, leads to a coalescing chamber 28 which is of a diameter to accommodate the elimination of the accumulation of air bubbles in the mercury contained in a manometer prior to its entry into the horizontal sample volume metering chamber 32 contained in housing 30 connected to stack 12.

The third main portion of the manometer 10 includes vent stack 46, which incorporates a vertical passage 56 therein leading to a vent outlet 76 around fitting 77. Communicating between vertical passage 56 and horizontal sample volume metering chamber 32 is a passage 50 leading to a valve containing chamber 52 containing one-way valve 54. Valve 54 is in the form of a ball valve for closing off passage 56, thus preventing the movement of mercury out of metering chamber 32, once the forward meniscus of the mercury contained in chamber 32 engages and moves valve 54 against its cooperating seat 55.

With respect to coalescing chamber 28, it has been found that passages with diameters smaller than 0.21 inches can entrap air bubbles between mercury segments. Therefore, coalescing chamber 28 is of a diameter of about 0.25 inches to provide the coalescing of the mercury therein prior to entry into chamber 32. Thus, no air will enter sample volume metering chamber 32.

Metering chamber housing 30 may be of a clear plastic material. Alternatively, it may contain a portion 33 thereof which is of a clear plastic in order to indicate visually the passage of mercury in metering chamber 32. Metering chamber 32 includes a start electrode 34, a stop electrode 36 and a ground contact 39. These electrodes are connected by leads 40, 38, respectively, and ground lead 42. These leads are connected to have the effect of controlling the metering function for controlling the time of passage of a sample through the scanning point of the instrumentation to which the manometer of the invention is connected, as will be understood by practitioners-in-the-art.

Once the mercury passes stop electrode 36 in metering passage 32, it passes into passage 50 which leads to chamber 52. The flow of mercury into the chamber 52 causes valve 54 to rise against seat 55 to shut off the flow of mercury. The capacity of chamber 52 can be controlled by nylon bolt 48 received therein in cooperation with washer 45. Passage 56 in vent stack 46 leads to vent chamber 90 which is defined by a top 44 cooperating with vent stack body 46. These parts are held together by bolts 17, as shown in FIG. 3. Positioned in chamber 90 is a diaphragm 70. This diaphragm 70 has the same properties as diaphragm 18 for containing mercury contained in vent stack 46. Diaphragm 70 is held in place by upper and lower cooperating O rings 72, 74 respectively.

Positioned in the upper portion of a vent stack 46 is a slide valve 66 shown both in FIGS. 1 and 3. Valve 66 has a passage 57 therein to provide communication between passage 56 and chamber 90 in its open position. Slide valve 66 moves to the left as viewed on FIG. 1 to a closed position so that it restricts the movement of mercury in the manometer during any shipping or handling procedures. A hole 68 in slide 66 may have a wire or other material pass therethrough in order to hold the slide in its closed position during shipping. As can be seen in both FIGS. 1 and 2 O rings 62, 64 serve to protect any leaking of mercury around the area of valve 66 in its movement in stack 46. Bolts 37 (FIG. 1) may be utilized to mount the manometer in position for use in a particle counter instrumentation facility.

Since the capacity of metering chamber 32 is, preferably, 0.2 milliliters between the start and stop electrodes, the slight tilt in the horizontal position thereof exactly compensates for the change in head in the 0.685 inch diameter supply well 24, as discussed above. Thus, the aperture vacuum is the same at the start of counting as at the end. This minimizes any effects of system volume compliance, as discussed above. Any variation in capacity of the metering chamber 32 will be small. For a 0.2 milliliter capacity the variation will be between plus 1.47% and minus 1.30%.

Thus, as will be appreciated from the above, the invention herein eliminates the need for a vacuum pump, vacuum regulator, vacuum bleed valves, a waste reservoir, waste reservoir electrodes with detection circuitry and alarm, a counting solenoid with count switch and timer circuitry. Moreover, there is no need to empty a waste reservoir, since there is none.

Illustrative of materials which may be used, in accordance with this invention for the diaphragms for the manometer include epichlorohydrin (Goodrich Hydrin 100), polyurethane or high acrylonitrile elastomers. Preferably, however, a butyl elastomer is used having a durometer of Shore 50, and a thickness within the range of between about 0.014 and 0.019 inches.

With regard to the housing of the manometer, preferably it will be of a clear plastic material such as an acrylic or an epoxy. The material must be inert to the materials being handled in the manometer. Other representative plastics include polysulfone, polystyrene or acrylonitrile-butadienestyrene terpolymer. Metal may also be used for the housings which metal must be inert to the materials being handled such as molybdenum or stainless steel. The sample volume tube 33 forming metering chamber 32 preferably is comprised of a borosilicate glass or quartz. Alternatively, chemically resistant glass or ceramic or chemically inert plastic may be utilized. It will be appreciated, that precision bore metal tubing or of inert material such as stainless steel could be utilized providing the electrodes are insulated from the tubing.

The electrodes may be comprised of, for example, molybdenum amalgam with mercury. With this arrangement, the content is a mercury-to-mercury contact which is self-renewing and reliable. Contact is at the wire tip with the remainder of any wire extending into the sample volume cavity being insulated with a varnish of some sort. Contact at the wire tip makes wire centering in the tube less critical and aids in maintaining accuracy.

While the forms of apparatus herein described constitute preferred embodiments of the invention, it is to be understood that the invention is not limited to these precise forms of apparatus, and that changes may be made therein without departing from the scope of the invention which is defined in the appended claims.

What is claimed is:

1. Manometer apparatus for metering successive equal quantities of a liquid suspension through instrumentation to which the manometer is connected, comprising
   (a) a housing with a vent opening at one end and a sample connection opening at the other end;
   (b) a passage in said housing extending from said vent opening to said sample connection opening;
   (c) a vertical mercury supply well in said passage adjacent said sample connection opening;
   (d) a substantially horizontal metering chamber in said passage defined by spaced apart start and stop electrodes positioned at the ends thereof; the improvement characterized by
   (e) a stretchable mercury impermeable, gas permeable diaphragm in each of said vent and sample connection openings;
   (f) said diaphragms being impermeable to sulfur containing gases;
   (g) leads for connecting said start and stop electrodes to instrumentation to which said manometer is to control;
   (h) said wire leads being simple wire leads extending to the axis of said metering chamber for engaging a mercury meniscus passing therethrough, and
   (i) said metering chamber being of a preset dimension between said start and stop electrode.

2. The apparatus of claim 1, further characterized by
   (a) a coalescing chamber in said passage between said vertical mercury supply well and said metering chamber;
   (b) said coalescing chamber being of a diameter of 0.25 inches to cause coalescing of any mercury moving therethrough and the removal of air bubbles therefrom.

3. The apparatus of claim 1, further characterized by
   (a) the capacity of said metering chamber is 0.2 milliliters, and
   (b) the diameter of said metering chamber is 0.066 inches.

4. The apparatus of claim 1, further characterized by
   (a) a tilt in said horizontal metering chamber from said start electrode to said stop electrode; and
   (b) said tilt offsetting the change in pressure in said passage caused by any displacement of said diaphragms at either end thereof.

5. The apparatus of claim 4, further characterized by
   (a) the capacity of said metering chamber being 0.2 milliliters; and
   (b) the diameter of said vertical mercury supply well being 0.685 inches.

6. The apparatus of claim 1, further characterized by
   (a) the tips of said wire leads adjacent the axis of said metering chamber being an amalgam of molybdenum and mercury; and
   (b) the remaining portion of said wire leads on said metering chamber being electrically insulated from said chamber.

7. The apparatus of claim 1, further characterized by
   (a) said diaphragms being a butyl elastomer having a durometer of Shore 50; and
   (b) said diaphragms having a thickness within the range of between about 0.014 and 0.019 inches.

8. The apparatus of claim 1, further characterized by
   (a) a one-way valve in said passage immediately downstream of said stop electrode; and
   (b) said one-way valve preventing movement of said mercury toward said vent opening after passing said stop electrode.

9. The apparatus of claim 8, further characterized by
   (a) said passage including a vertical vent stack downstream of said stop electrode;
   (b) said one-way valve in said vent stack; and
   (c) said vent opening and vent opening diaphragm positioned in the top of said vent stack.

* * * * *